United States Patent [19]

Newberry

[11] Patent Number: 5,015,182

[45] Date of Patent: May 14, 1991

[54] DENTAL FIXATOR APPARATUS

[76] Inventor: Norman E. Newberry, 1736 Chateau Ave., Anaheim, Calif. 92804

[21] Appl. No.: 448,901

[22] Filed: Dec. 12, 1989

[51] Int. Cl.⁵ .............................................. A61C 11/00
[52] U.S. Cl. ........................................ 433/60; 433/61; 433/63
[58] Field of Search ...................... 433/54, 60, 61, 63, 433/65, 66

[56] References Cited

U.S. PATENT DOCUMENTS

| | | | |
|---|---|---|---|
| 772,304 | 10/1904 | Williams | 433/65 |
| 1,102,741 | 7/1974 | Hardie | 433/60 |
| 1,485,657 | 3/1924 | Williams | 433/60 |
| 2,765,533 | 10/1956 | McMorris | 433/65 |
| 2,930,127 | 3/1960 | Mann et al. | |
| 3,059,336 | 10/1962 | Windish | |
| 3,758,096 | 9/1973 | Tregillis et al. | |
| 4,200,981 | 5/1980 | Fine | 433/60 |
| 4,412,822 | 11/1983 | Blechner | 433/60 |
| 4,480,995 | 11/1984 | Tate | 433/54 |

Primary Examiner—Cary E. Stone
Attorney, Agent, or Firm—Henry M. Bissell

[57] ABSTRACT

A dental fixator device includes a vertical staff, an upper horizontal arm, a lower horizontal arm, and a pair of clamps on each of the two arms, one of the clamps of each arm being adjacent the rear thereof and slidable on a jig towards the front clamp of the arm, each pair of clamps thereby holding releasably a dental model or cast against the associated arm. The clamps can be pivoted in a horizontal plane and include barrel-shaped serrated gripping surfaces on opposite ends thereof. Each arm has a front flange through which a longitudinal screw runs to the jig for moving the jig along the arm. The upper arm is connected to a cylinder, in turn connected to the staff so that the arm can be rotated around its longitudinal axis. The front end of the cylinder may be pivotably connected to the upper arm and locked in position at a selected angle to the cylinder to accommodate work on the dental models or casts borne on the arms. A vertical reference stop collar can be releasably secured to the staff between the arms. The device provides improved multi-directional adjustability.

6 Claims, 3 Drawing Sheets

DENTAL FIXATOR APPARATUS

BACKGROUND OF THE INVENTION

1. Field of the Invention

The present invention relates generally to dental appliances and more particularly to a device for aligning and holding dental models or casts in such alignment during use in the fabrication of orthodontic and functional appliances.

2. Description of the Related Art

Dental cast holders are used in the production of dental restorations, for example, dental models or casts, inlays, bridges, crowns and the like; that is, both orthodontic and functional appliances. Most such fixators or holders comprise a vertical rod connected to two vertically spaced horizontal arms or frames to which the dental models or casts are secured by a gypsum bonding agent which takes 15 to 30 minutes to harden. Once the bonding agent is hardened in place, the models or casts cannot be removed without removing the bonding agent.

The alignment holders shown in, for example, U.S. Pat. Nos. 3,059,336 to Windish and 3,758,096 to Tregillis et al, as well as U.S. Pat. Nos. 4,412,822 to Blechner, 4,480,995 to Tato, 1,102,741 to Hardie and 2,930,127 to Mann et al represent the state of the art, the holders disclosed therein generally conforming to the description given above. Such holders unfortunately do not permit rapid and accurate processing of orthodontic and functional dental appliances. They do not have a degree of adjustability which would simplify the manufacturing process for the appliance.

Accordingly, there is a need for a simple dental fixator device which is inexpensive, durable and efficient, which shortens the dental appliance manufacturing time and which provides greater adjustability and flexibility than those currently available. Preferably, such a holder should incorporate means which would eliminate the necessity of using slow-hardening gypsum bonding agent to hold dental casts or models, supporting molds and the like in place in the holder. Such casts or models and molds should be easily removable and realignable in the holders.

SUMMARY OF THE INVENTION

The improved dental fixator device of the present invention satisfies all the foregoing needs. The device is simple, durable, efficient and compact, and obviates the necessity for the use of gypsum bonding agent or the like to hold the dental appliance, supporting matrix, mold or cast body in place in the holder. Such items can be removed, adjusted and reinserted in the holder rapidly and easily, being returned to the same orientation as before. The device is substantially as set forth in the Abstract of the Disclosure.

The improved fixator device of the present invention includes a vertical staff or post, to which are connected vertically spaced upper and lower horizontal arms. The arms each bear a pair of spaced clamps. One clamp is connected to the free front end of the arm along with a fixed flange, while the other clamp is connected to a jig riding in a longitudinal slot in the arm and advanced along the arm by a lead screw passing through the fixed flange and the jig.

The upper arm is adjustably secured to the staff by a cylindrical shaft which permits the arm to be rotated to a desired position around its longitudinal axis and then be pinned in place. The front end of the shaft is pivoted to the rear end of the upper arm by a locking screw for locking the arm in a selected angular plane relative to the cylindrical shaft angle. The contacting surfaces of the pivot joint are frictionally engaged once the locking screw is tightened down so that the selected angle of the upper arm is maintained during work on the dental appliances in the device.

The staff bears a vertical reference collar releasably pinned thereto, as is the lower arm, and is preferably rectangular, with the upper arm connected via the shaft to a locking block on the top of the staff. Each clamp is a bracket bearing barrel-shaped serrated dental cast or model or mold-gripping surfaces on opposite ends thereof and is secured by a vertical pin to the arm for rotation in a horizontal plane and then locking in place. This enables each appliance, supporting mold and the like to be securely and releasably held in the device without the use of bonding agents, so that the appliance can be removed from the device and reinserted, as needed.

BRIEF DESCRIPTION OF THE DRAWING

A better understanding of the present invention may be realized from a consideration of the following detailed description, taken in conjunction with the accompanying drawing in which.

DESCRIPTION OF THE PREFERRED EMBODIMENT

Figure 1:
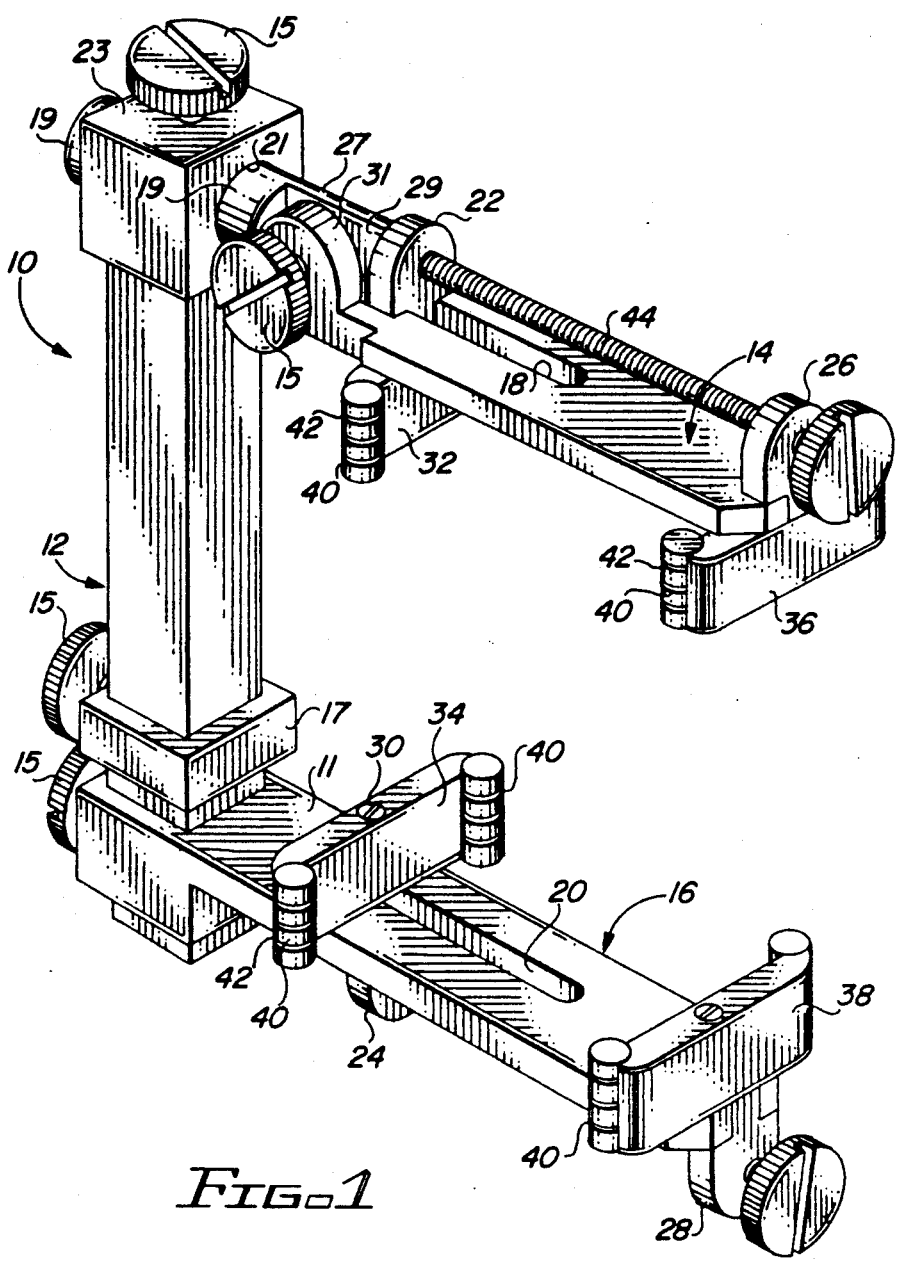
FIG. 1 is a schematic perspective view of a preferred embodiment of the improved dental fixator device of the present invention.
Figure 2:
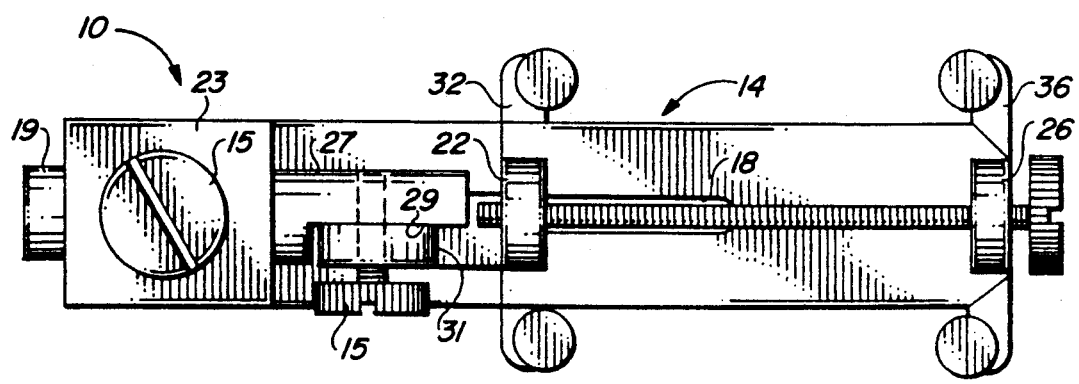
FIG. 2 is a schematic top plan view of the device of FIG. 1.

Now referring more particularly to the accompanying drawings, FIGS. 1-4 schematically depict a preferred embodiment of the improved dental fixator device of the present invention. Thus, device 10 is shown which comprises a preferably rectangular vertical staff or post 12 to which are releasably connected upper and lower horizontal arms 14 and 16 spaced above one another and parallel to each other.

Each arm 14 and 16 comprises a flattened bar with a slot, numbered 18 in the case of arm 14 and 20 in the case of arm 16, vertically therethrough and extending longitudinally thereof. The rear end of slot 18 is open, while that of slot 20 is closed. Both slots are near the rear of their arms.

The rear end 11 of arm 16 has a vertical opening 13 through which staff 12 fits so that arm 16 can slide up and down thereon. Arm 16 is releasably secured in place by a locking screw 15. An identical screw 15 releasably secures vertical reference stop collar 17 in place on staff 12 above arm 16 below arm 14.

Arm 14 is releasably secured to staff 12 by a cylindrical shaft 19, the rear end of which is releasably secured by a locking screw 15 in an opening 21 in an upper locking block 23 held on the top of staff 12 by an allen screw 25. The front end 27 of shaft 19 is flattened to provide a vertical slightly concave surface 29 releasably locked to a rear connecting cantilever flange 31 by a transversely extending locking screw 15. With this arrangement arm 14 can be removed from connection to shaft 19, if desired, and can be securely held at a selected angle relative to the orientation of shaft 19 when the locking screw 15 is tightened so that the mutually contacting faces of shaft 19 and arm 14 are frictionally engaged.

A jig comprising an upstanding flange 22 is slideably disposed in slot 18 and projects above arm 14, while a jig comprising a similar flange 24 depends from arm 16 and slides in slot 20. The free front end of arm 14 bears a fixed upstanding flange 26 while the free front end of arm 16 bears a fixed depending flange 28. Flanges 22 and 24 are releasably secured, as by screws 30, to the center of brackets 32 and 34, respectively, while flanges 26 and 28 are releasably connected by screws 30 to, respectively, brackets 36 and 38 identical to brackets 32 and 34. Brackets 32, 34, 36 and 38 each comprise flat upstanding plates disposed transversely of arms 14 and 16 and bearing on opposite ends thereof barrel-shaped protrusions 40 having gripping surfaces 42. Protrusions 40 of brackets 32 and 36 face each other, as do protrusions 40 of brackets 34 and 38.

Figure 3:
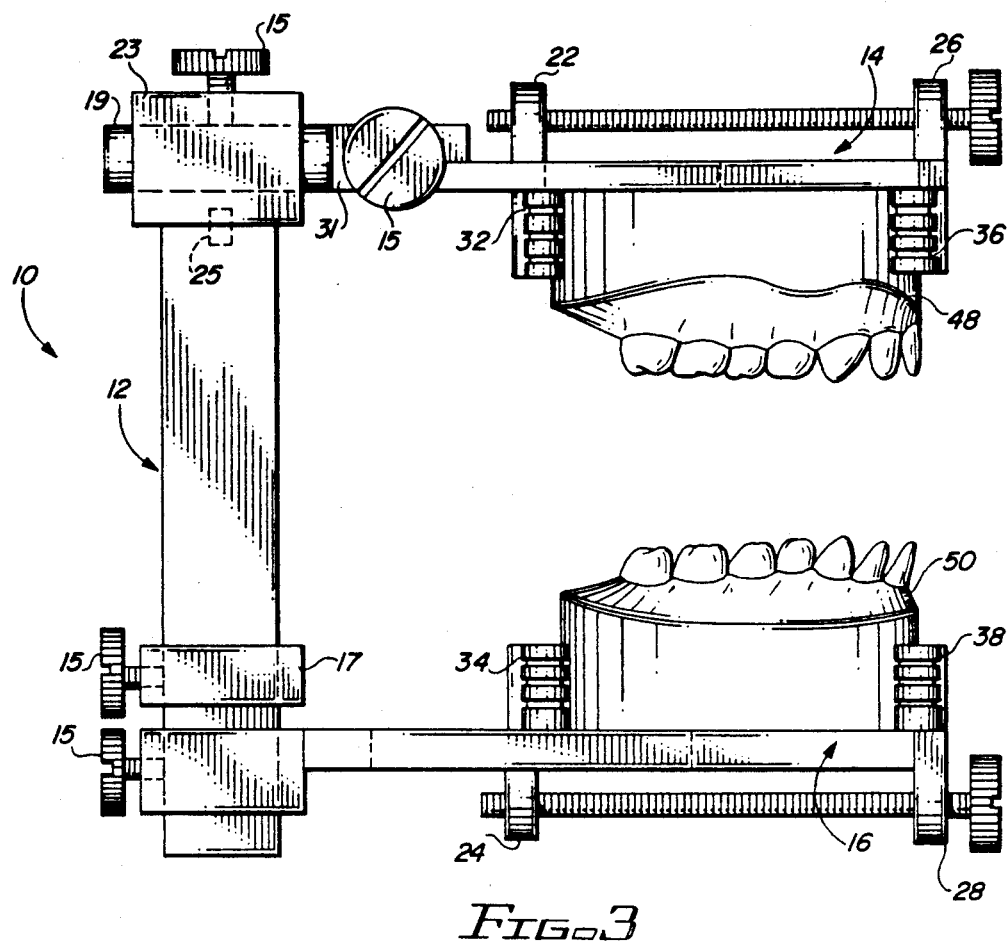
FIG. 3 is a schematic side elevation of the device of FIG. 1, shown with a pair of dental models or casts and supporting molds in place in the device.
Figure 4:
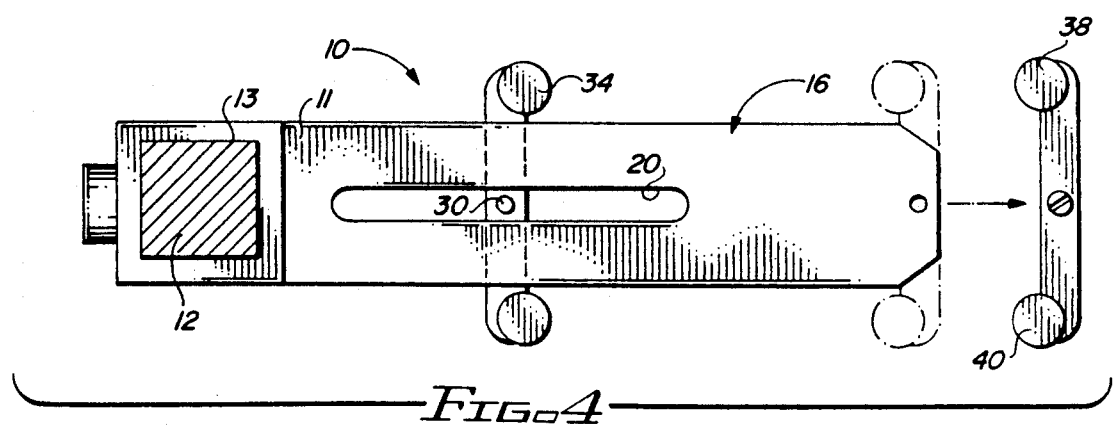
FIG. 4 is a schematic bottom plan view of the device of FIG. 1, shown with the clamps thereof removed.
Figures 5, 5A:
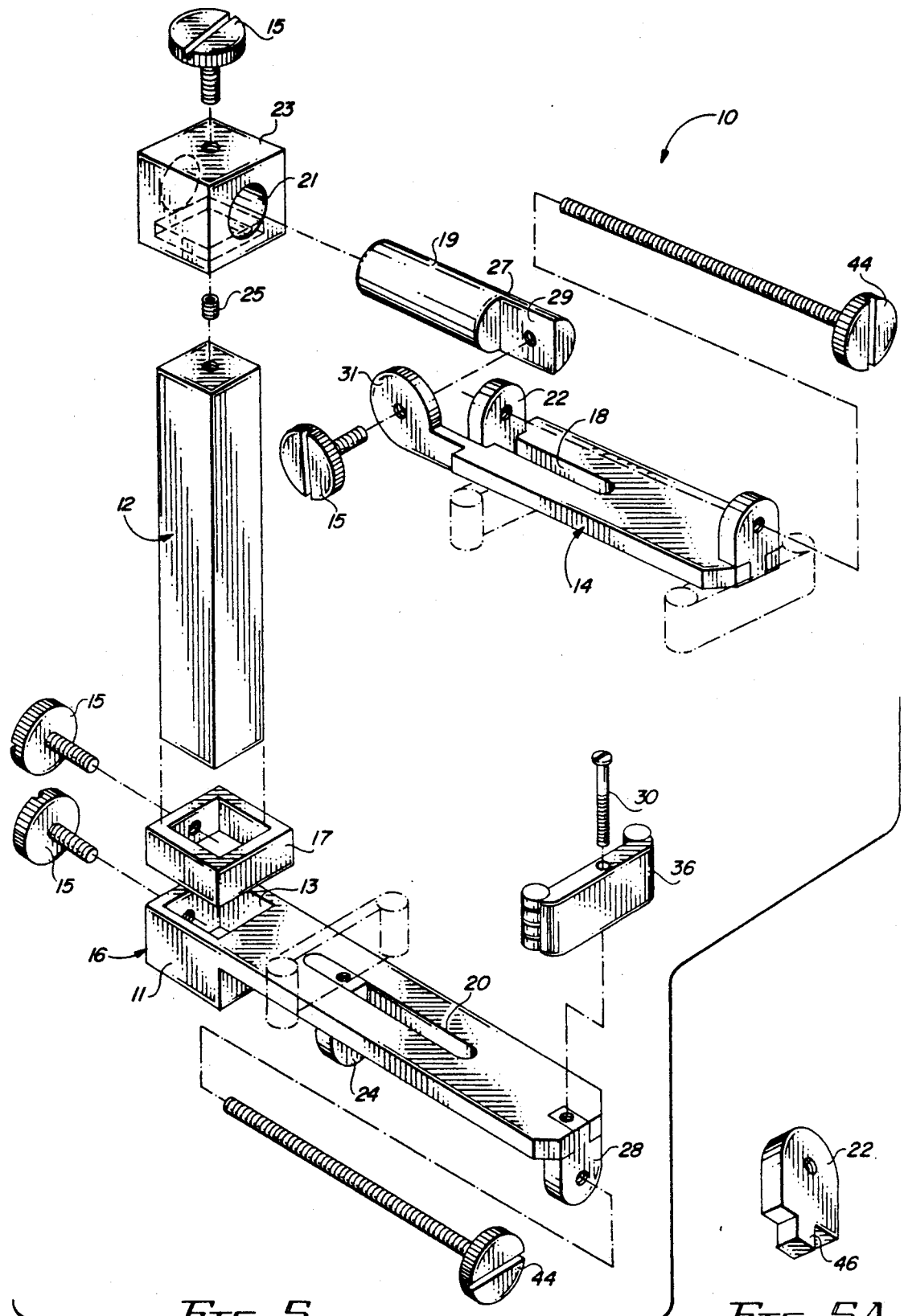
FIG. 5 is an exploded view of the device of FIG. 1, FIG. 5A showing a detail, namely, the outer clamping flange used in the device of FIG. 1.

Brackets 32 and 36 depend from arm 14, while brackets 34 and 38 project up above arm 14. Long adjustment screws 44 extend longitudinally of arms 14 and 16 through flanges 22, 24, 26 and 28, as shown in FIG. 3, to cause flanges 22 and 24 to travel along slots 18 and 20, bearing brackets 32 and 34. It will be noted that the flanges all have protruding tongues 46 (FIG. 5A) which in the case of flanges 22 and 24 ride in slots 18 and 20 as brackets 32 and 34 are moved towards brackets 36 and 38 in order to firmly releasably grip dental models or casts 48 and 50 (FIG. 3) therebetween.

It will be noted that the clamps represented by the described brackets can pivot in a horizontal plane so as to be able to tightly grip casts 48 and 50, whatever their contour. Moreover, casts 48 and 50 can be run into contact with each other by unlocking arm 16 and running it up staff 12, then locking it in place. Brackets 32 and 34 can then be backed off of casts 48 and 50 by long screws 44, casts 48 and 50 can then be rotated as a unit to a new work position, brackets 32 and 34 can be moved to regrip casts 48 and 50 and then arm 16 can be run down staff 12 to a desired position. This enables work to be carried out on casts 48 and 50, while in device 10, from various positions and angles without the use of gypsum bonding agent or any other bonding agent. Accordingly, work with the use of device 10 is more rapid, precise and efficient.

Collar 17 enables arm 16 to be precisely repositioned and cross-checked for slippage as work progresses. The pivoting action of arm 14 facilitates access to casts 48 and 50 while in device 10 and the ability of arm 14 to be rotated around its longitudinal axis, due to the cylindrical nature of shaft 19 in locking block 23, acting in concert with the cantilever pivoting action of arm 14, enables dental casts to be precisely positioned in device 10. Because surface 29 is slightly concave and preferably formed of stainless steel while flange 31 is preferably aluminum, the necessary gripping and locking action between surface 29 and flange 31 assures that arm 14 will not shift once it is locked in place by transverse locking screw 15.

Although device 10 is simple, durable and inexpensive, it also is highly efficient, affording an adjustability of components not previously obtained with dental fixators. This results in improved dental models or casts more precisely and more rapidly and economically crafted. Device 10 can be fabricated of any suitable conventional materials, including metal, ceramic, cermet, reinforced plastic and the like, preferably a durable metal such as stainless steel and the like, and with dissimilar metals for the flange 31 and shaft surface 29, as previously described.

Although there have been described hereinabove specific arrangements of a dental fixator apparatus in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A dental fixator device comprising, in combination:
    (a) a vertical staff;
    (b) an upper horizontal arm adapted to support a dental model or cast;
    (c) a horizontal shaft, the front end of which is releasably secured to the rear end of said upper horizontal arm and the rear end of which is releasably secured to said staff adjacent the upper end thereof, whereby said arm can be rotated around the longitudinal axis thereof and held in a desired position;
    (d) a lower horizontal arm releasably secured to said staff below said upper arm and adapted to slide vertically on said staff and to support a dental model or cast; and
    (e) two spaced pairs of clamps, one said pair being connected to one of said horizontal arms and the other of said paris being connected to the other of said horizontal arms, one clamp of each said pair being adjacent the rear of and slidable longitudinally of the associated horizontal arm, whereby a dental model or cast can be releasably held by the clamps of said pair without the use of bonding agent, each said clamp comprising a bracket, the opposite ends of which bear expanded gripping surfaces, each of said bracket being pivotally locked to the associated arm by a vertical screw for adjustable rotation in a horizontal plane, the brackets of said upper arm depending therefrom while the brackets of said lower arm project upwardly therefrom.

2. The device of claim 1 wherein each said arm has a jig connected to one of said clamps and sliding in a longitudinal groove in said arm, wherein the front end of said arm has the other of said clamps, and a flange through which a longitudinal adjusting screw is trained, said screw also being connected to said jig for movement of said jig and associated clamp towards and away from said front clamp, thereby releasably gripping said dental model or cast.

3. The device of claim 2 wherein said jig and flange of said upper arm project upwardly therefrom, while said jig and flange of said lower arm depend therefrom.

4. A dental fixator device comprising, in combination:
    (a) a vertical staff;
    (b) an upper horizontal arm adapted to support a dental model or cast;

(c) a generally cylindrical horizontal shaft, the front end of which is flattened and is releasably secured to a rear flange of said upper horizontal arm by a transverse releasable locking means, whereby said upper arm can be locked in place at a selected angle relative to the orientation of said shaft, and the rear end of which shaft is releasably secured to said staff adjacent the upper end thereof, whereby said arm can be rotated around the longitudinal axis thereof and held in a desired position;

(d) a lower horizontal arm releasably secured to said staff below said upper arm and adapted to slide vertically on said staff and to support a dental model or cast; and (e) two spaced pairs of clamps, one said pair being connected to one of said horizontal arms and the other of said pairs being connected to the other of said horizontal arms, one clamp of each said pair being adjacent the rear of and slidable longitudinally of the associated horizontal arm, whereby a dental model or cast can be releasably held by the clamps of said pair without the use of bonding agent.

5. The device of claim 4 wherein said shaft front end has a generally vertical slightly concave surface against which said rear flange bears, wherein said shaft is of stainless steel and said rear flange is of aluminum to increase the frictional resistance therebetween, and wherein said transverse releasable locking means is a locking screw.

6. A dental fixator device comprising, in combination:

(a) a generally rectangular vertical staff having a vertical reference collar releasably secured thereto;

(b) an upper horizontal arm above said collar and adapted to support a dental model or cast;

(c) a horizontal shaft, the front end of which is releasably secured to the rear end of said upper horizontal arm and the rear end of which is releasably secured to said staff adjacent the upper end thereof, whereby said arm can be rotated around the longitudinal axis thereof and held in a desired position;

(d) a lower horizontal arm below said collar and releasably secured to said staff below said upper arm and adapted to slide vertically on said staff and to support a dental model or cast;

(e) an upper locking block releasably secured to the upper end of said staff, through which said shaft passes; and, (f) two spaced pairs of clamps having barrel-shaped and serrated gripping surfaces, one said pair being connected to one of said horizontal arms and the other of said pairs being connected to the other of said horizontal arms, one clamp of each said pair being adjacent the rear of and slidable longitudinally of the associated horizontal arm, whereby a dental model or cast can be releasably held by the clamps of said pair without the use of bonding agent.

* * * * *